United States Patent [19]

Yamada et al.

[11] Patent Number: 4,906,768

[45] Date of Patent: Mar. 6, 1990

[54] PROCESS FOR PRODUCTION OF OXIME DERIVATIVES

[75] Inventors: Toshiro Yamada, Fujisawa; Jiro Tsuji, Kamakura; Kuniaki Goto, Tokyo, all of Japan

[73] Assignee: Nippon Zeon Co., Ltd., Tokyo, Japan

[21] Appl. No.: 157,173

[22] Filed: Feb. 11, 1988

Related U.S. Application Data

[63] Continuation of Ser. No. 836,138, Mar. 4, 1986, abandoned.

[30] Foreign Application Priority Data

Mar. 6, 1985 [JP] Japan .................................. 60-44192
Mar. 6, 1985 [JP] Japan .................................. 60-44193
Jul. 31, 1985 [JP] Japan .................................. 60-169098

[51] Int. Cl.$^4$ .................. C07C 131/00; C07C 131/02
[52] U.S. Cl. ...................................... 560/32; 564/253; 564/258; 564/265; 564/267; 564/268; 560/122

[58] Field of Search ....................... 564/253, 256, 264; 562/258, 265, 267, 268; 560/32, 122

[56] References Cited

PUBLICATIONS

European Search Report, EP-86102811, dated Mar. 26, 1987.
Gant, Patricia A. et al., *J. Chem. Soc. Perkin Trans. I* (1974) pp. 1835–1839.
McOmie, J. F. W. *Protective Groups in Organic Chemistry* (1973) Plenum Press London pp. 96–99 and 411.

*Primary Examiner*—Michael L. Shippen
*Attorney, Agent, or Firm*—Sherman and Shalloway

[57] ABSTRACT

A process for producing an oxime derivative, which comprises protecting the hydroxyimino group of an oxime compound with a protecting agent, subjecting the protected oxime compound to a given reaction, and thereafter deprotecting the reaction product, wherein a 2-alkenylating agent is used as the protecting agent.

26 Claims, No Drawings

PROCESS FOR PRODUCTION OF OXIME DERIVATIVES

This application is a continuation of application Ser. No. 836,138 filed Mar. 4, 1986, now abandoned.

This invention relates to a process for producing oxime derivatives. More specifically, this invention relates to the production of an oxime derivative which utilizes a new method of protecting a starting oxime compound whereby protection and deprotection can be performed by simple operations and the protected compound is stable under various reaction conditions.

Oxime compounds undergo various peculiar reactions under various reaction conditions because they have a hydroxyl group with relatively high activity. In an attempt to avoid such reactions, it has been proposed to protect an oxime compound as a benzyl ether [Helv. Chim. Acta, 60, 2294 (1977)] or to protect it with a phenyl thiomethyl ether [J. Org. Chem., 38. 3749 (1973).] According to the former method, an oxime compound having a double bond cannot be used as a stating material because catalytic hydrogenation is essential in deprotection. The latter method is difficult to use in practice because it requires a large amount of a mercury salt for deprotection.

It is an object of this invention to remove these technical defects of the prior art. The present inventors have undertaken extensive investigations in order to achieve this object, and have found that when the hydroxyimino group of an oxime compound is converted into a 2-alkenyloxyimino group, the resulting product is stable to various reactions, and also can be easily deprotected.

Thus, according to this invention, there is provided a process for producing an oxime derivative, which comprises protecting the hydroxyimino group of an oxime compound with a protecting agent, subjecting the protected oxime compound to a given reaction, and thereafter deprotecting the reaction product, wherein a 2-alkenylating agent is used as the protecting agent.

The oxime compound used in this invention has at least one hydroxyimino group and at least one other functional group. The functional group, as used herein, denotes a functional group which does not adversely affect a reaction of protecting the hydroxyimino group and has higher activity than the 2-alkenyloxyimino group under reaction conditions for producing a protected oxime derivative.

Specific examples of the functional group include a hydroxyl group, an amino group, a cyano group, a sulfonyl group, a sulfone group, an ether linkage, a thioether linkage, and an acid amide linkage.

When a lower fatty acid or its salt is used as a nucleophilic reagent in deprotection, the starting oxime compound may further contain a carbonyl group, an epoxy group, an ester linkage (including lactones), an acetal linkage, a chlorine atom, etc. The desired deprotecting reaction may be carried out by using other nucleophilic reagents, but the reaction between the above functional groups and the nucleophilic reagents must be taken into consideration.

When the functional group includes a hydroxyl group or an amino group, the hydroxyamino group can be selectively protected because such a group less reactive with the 2-alkenylating agent than the hydroxyimino group. When the functional group includes a group having higher reactivity than the hydroxyimino group, such as a carboxyl group, the desired protected oxime derivative can be obtained by 2-alkenylating both of these groups, and thereafter reacting only the more reactive 2-alkenyloxycarbonyl group.

The oxime compound may be of any of the aliphatic, alicyclic, aromatic and heterocyclic structures, and may contain a carbon-carbon double bond or a carbon-carbon triple bond in the molecule. The molecular weight of the oxime compound does not greatly affect the reaction. But usually, it has a molecular weight of not more than 5,000, and particularly contains not more than 100 carbon atoms, preferably not more than 50 carbon atoms.

There is no particular restriction on the method of converting the hydroxyimino group into a 2-alkenyloxyimino group, and it can be carried out in a customary manner. For example, for introduction of an allyl group, it is known to react the oxime compound with an allyl halide typified by allyl bromide in a suitable solvent such as tetrahydrofuran using a base such as sodium methylate [Zh. Org. Khim., 4, 567 (1968)], or to carry out the above reaction in a mixture of water and a hydrophobic organic solvent such as benzene in the presence of both a base such as sodium hydroxide and a phase transfer catalyst such as a tetraalkyl ammonium halide [Chem. Lett., 869 (1980)].

The 2-alkenylating agent used in this invention may be any compound which reacts with the hydroxyimino group to convert it into a 2-alkenyloxyimino group. Usually preferred is a compound of the following general formula

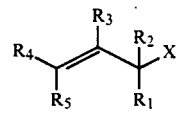

wherein each of $R_1$, $R_2$, $R_3$, $R_4$ and $R_5$ represents hydrogen or a hydrocarbon group which may have a substituent, and X represents a halogen atom such as chlorine, bromine or iodine, or a residue of a sulfonic acid such as p-toluenesulfonic acid or methanesulfonic acid.

In the above formula, specific examples of the 2-alkenyl group are an allyl group, a methallyl group, a crotyl group, a cinnamyl group, a prenyl group, a 2-pentenyl group, a 2-ethyl-2-butenyl group, a p-chloro-cinnamyl group, a geranyl group, a neryl group, and lower alkoxy derivatives of these groups.

The number of carbon atoms of the 2-alkenyl group can be properly chosen by considering the ease of separating the alkene formed by the deprotection reaction, the ease of obtaining the starting material, etc. Usually, it is not more than 10. When the 2-alkenyl group has not more than 5 carbon atoms, the by-product alkene can be removed in gaseous form from the reaction system.

The resulting oxime compound having the 2-alkenyloxyimino group (i.e., protected oxime compound) is then subjected to a given reaction utilizing the other functional group of the compound to form a protected oxime derivative. The reaction may be any of reactions known heretofore with regard to oxime compounds protected with a benzyl ether, etc.

O-alkylation is carried out, for example, by reacting a protected oxime compound having a hydroxyl group with an alkyl halide in a suitable solvent such as tetrahydrofuran using a base such as sodium hydride.

The reaction of converting the amino group into a carbamate group is carried out by reacting a protected oxime compound having the amino group with a halogenocarbonic ester in a suitable solvent such as acetone in the presence of a base such as sodium hydrogen carbonate.

An oxidation reaction may, for example, be carried out by oxidizing a protected oxime compound having a hydroxyl group with an oxidizing agent such as a Jones' reagent (a mixture of chromic anhydride and dilute sulfuric acid) at 0° C. to room temperature in a polar solvent such as acetone to convert it into a carboxylic acid or a ketone.

C-alkylation may, for example, be carried out by reacting a protected oxime compound having a carbonyl group with an alkyl metal such as methylmagnesium bromide at room temperature or below in a solvent such as diethyl ether to give an alkylated protected oxime derivative.

The reaction of converting the hydroxyimino group into a carbonyl group may be carried out, for example, by stirring a protected oxime compound having a non-protected hydroxyimino group in addition to a protected hydroxyimino group at room temperature in a mixed solvent of water and methanol in the presence of a reducing agent, such as an excess of titanium trichloride, and ammonium acetate to convert it into a protected oxime derivative having a carbonyl group.

As an example of reduction, a protected oxime compound having a carbonyl group is reacted with a reducing agent such as sodium borohydride in water-methanol to give a corresponding protected oxime derivative having a hydroxyl group.

It is known that an oxime compound not protected with the 2-alkenyl group, when placed under the conditions of the reactions illustrated above, undergo conversions corresponding to the individual reactions.

There is no particular limitation on the reaction conditions, and those conditions which are generally used in a particular desired reaction may be applied as such.

The protected oxime derivative so obtained is then converted into the desired oxime derivative by deprotection of the 2-alkenyl group.

There is no particular limitation on the technique of deprotection. Conveniently, the deprotection is carried out by using a catalyst consisting essentially of a compound of a platinum-group metal, preferably a compound of a platinum-group metal and a ligand. The platinum-group metal compound may include salts or complexes of palladium, ruthenium, platinum and rhodium. Specific examples are tris(dibenzylideneacetone)-dipalladium (O), tris(tribenzylideneacetylacetone)-tripalladium (O), tetrakis(triphenylphosphine)palladium (O), palladium acetate, palladium propionate, palladium butyrate, palladium benzoate, palladium acetylacetonate, palladium nitrate, palladium sulfate, palladium chloride, dihydrotetrakis(triphenylphosphine)ruthenium, ruthenium acetylacetonate, platinous acetate and platinum acetylacetonate.

Of these, palladium compounds are preferred in view of their reactivity. It is especially preferred to use O-valent palladium olefin complexes or divalent organic palladium compounds.

The ligand used is an electron donor compound having a metal of Group V of the periodic table, i.e. nitrogen, phosphorus, arsenic or antimony, as a coordination atom. Specific examples include nitrogen-containing compounds such as pyridine, quinoline, trimethylamine, triethylamine, tributylamine, $\alpha,\alpha'$-dipyridyl and 1,10-phenanthroline; phosphorus-containing compounds such as triethylphosphine, tri-n-butylphosphine, triphenylphosphine, tri-o-tolylphosphine, tri-p-biphenylphosphine, tri-o-methoxyphenylphosphine, phenyldiphenoxyphosphine, triethyl phosphite, tri-n-butyl phosphite, tri-n-hexyl phosphite, triphenyl phosphite, tri-o-tolyl phosphite, triphenyl thiophosphite, $\alpha,\beta$-ethylenedi(diphenyl)phosphine, $\alpha\beta$-ethylenedi(diethyl)phosphine and $\alpha,\beta$-ethylenedi(dibutyl)phosphine; arsenic-containing compounds such as triethylarsenic, tributylarsenic or triphenylarsenic; and antimony-containing compounds such as tripropylantimony and triphenylantimony. Of these, the phosphorus-containing compounds are preferred in view of their activity and selectivity in the reaction and economy.

The amount of the ligand used is usually at least 0.1 mole per mole of the platinum-group metal compound, and from the viewpoint of its activity in the reaction, it is preferably at least 1 mole, especially 2 to 20 moles.

The amount of the catalyst can be properly chosen, and it is generally used in such a proportion that the amount of the platinum-group metal compound is 0.01 to 10 moles, preferably 0.1 to 5 moles, per 100 moles of the protected oxime derivative. This amount is for a material having one 2-alkenyloxyimino group, and the amount of a material having two or more 2-alkenyloxyimino groups is increased according to the number of the -alkenyloxyimino groups. The platinum-group metal compound and the ligand may be reacted in advance, but usually, the catalyst is prepared in situ by contacting the individual components in the reaction system.

The deprotection reaction using the platinum-group metal compound as a catalyst is carried out in the presence of a nucleophilic agent. Specific examples of the nucleophilic agent include lower fatty acids or its salts, alkali metal salts of phenols and alkali metal salts of 1,3-dicarbonyl compounds.

Specific examples of the lower fatty acids are formic acid, acetic acid and propionic acid. Specific examples of their salts include ammonium salts or amine salts such as ammonium formate, pyridine formate, morpholine formate, monomethylamine formate, diethylamine formate, trimethylamine formate, diethylamine formate, trimethylamine formate, triethylamine formate, triethanolamine formate, ammonium acetate, ammonium propionate, triethylamine acetate, triethylamine propionate, pyridine acetate, monomethylamine propionate and monoethanolamine acetate; and metal salts such as sodium formate, calcium formate, sodium acetate, potassium acetate, potassium propionate and calcium acetate.

Specific examples of the alkali metal salts of phenols are sodium phenoxide, sodium methylphenoxide, potassium phenoxide and potassium methylphenoxide.

Specific examples of the alkali metal salts of 1,3-dicarbonyl compounds are a sodium salt of methyl acetoacetate, a lithium salt of ethyl acetoacetate, a sodium salt of dimethyl malonate, a potassium salt of diethyl malonate, a sodium salt of ethyl 2-oxocyclopentanecarboxylate, a sodium salt of cyclohexane-1,3-dione, and a potassium salt of dimedone.

Among these nuclophilic reagents, the formic acid compounds, particularly organic amine salts of formic acid, are preferred in view of their reactivity and operability.

The amount of the nucleophilic reagent can be properly chosen, and is usually at least one molecule, preferably 2 to 10 molecules, per protected oxime in the protected oxime derivative.

The deprotection reaction is carried out by contacting the protected oxime derivative with the catalyst in the presence of the nucleophilic reagent. By this reaction, the protected hydroxyimino group is removed, and simultaneously, the 2-alkenyl group is combined with the nucleophilic reagent to give an alkenyl-type by-product. The reaction temperature is usually at least 20° C., preferably 50° to 150° C. The reaction time is usually 5 minutes to 24 hours.

The reaction may be carried out in the further presence of a diluent. Specific examples of the diluent are nitriles such as acetonitrile, propionitrile, butyronitrile and benzonitrile; amides such as dimethylformamide, diethylformamide, dimethylacetamide, dimethylpropionamide and N-methylpyrrolidone; ethers such as tetrahydrofuran, dioxane, dibutyl ether and ethylene glycol dimethyl ether; alcohols such as methanol, ethanol, propanol, tert-butanol, ethylene glycol and diethylene glycol monoethyl ether; sulfoxides such as dimethyl sulfoxide and diethyl sulfoxide; and hydrocarbons such as n-hexane, cyclohexane, benzene, toluene and xylene. Of these, the nitriles, amides, ethers and alcohols are preferred. Water may be added to the diluent in order to increase the compatibility between the nucleophilic reagent and the protected oxime derivative.

The diluent is used usually in such a proportion that the concentration of the protected oxime derivative is 1 to 50 % by weight. The use of the diluent can lead to an increase in the activity of the reaction and the stability of the catalyst.

After the reaction, the reaction mixture is worked up by conventional methods, for example by extraction, distillation or recrystallization to give the desired oxime derivative of high purity.

The oxime derivatives obtained by the process of this invention may be various aliphatic, alicyclic, aromatic or heterocyclic compounds and are useful, for example, as industrial chemicals, medicines, agricultural chemicals and intermediates of these.

Thus, the present invention provides a simple, convenient and practical process which can also be applied to the protection of oxime compounds having a double bond which has previously been difficult.

The following examples illustrate the present invention more specifically.

EXAMPLE 1

Allyl etherification

A reactor was charged with 1 mole of 2-methyl-5-hydroxyimino-2-heptene, 8 moles of methanol containing 1.2 moles of sodium methylate, and 10 moles of tetrahydrofuran (THF). The mixture was cooled to 0° C., and with stirring, 1.3 moles of allyl bromide was added dropwise over 5 minutes. The mixture was stirred at room temperature for one day. The reaction mixture was concentrated, and 40 parts of methylene chloride was added. The mixture was washed with water, and the solvent was evaporated. The residue was purified by silica gel column chromatography to give 2-methyl-5-allyloxyimino-2-heptene in a yield of 80 mole %. Identification of this compound was performed by using IR, NMR and mass spectra (the same techniques were used to identify compounds appearing hereinafter).

Deprotection

An aliquot (0.5 mole) of the resultinge compound was reacted under stirring for 1 hour together with 0.005 mole of palladium acetate, 0.02 mole of tripenylphosphine, 1.5 moles of triethylamine formate, 20 moles of ethanol and 12 moles of water. After the reaction, ethanol was evaporated from the reaction mixture under reduced pressure. Ten moles of methylene chloride was added to the residue, and the mixture was washed with water. The solvent was evaporated, and the residue was purified by silica gel column chromatography to give 2-methyl-5-hydroxyimino-2-heptene in a yield of 96 mole %. A quantitative analysis of the reaction mixture by gas chromatography showed that the reaction proceeded quantitatively.

The results demonstrate that the allyl etherification of an oxime compound is an effective protecting method and can be applied also to compounds having a carbon-carbon double bond.

EXAMPLE 2

Allyl etherification (synthesis of a protected oxime compound)

The same allyl etherification procedure as in Example 1 was repeated except that 3-hydroxyiminobutanol was used as a starting material. 3-Allyloxyiminobutanol was obtained in a yield of 75 mole %.

Benzyl etherification of the hydroxyl group (synthesis of a protected oxime derivative)

A reactor was charged with 0.1 mole of 3-allyloxyiminobutanol, 0.12 mole of benzyl chloride and 2 moles of THF. The mixture was cooled to 0° C., and 0.11 mole of sodium hydroxide was added little by little. The temperature of the mixture was returned to room temperature, and it was stirred for 2 hours. After the reaction, the product was isolated in a customary manner to give 3-allyloxyiminobutyl benzyl ether in a yield of 95 mole %.

Deprotection (synthesis of an oxime derivative)

The same deprotecting procedure s in Example 1 was repeated except that 3-allyloxyiminobutyl benzyl ether was used as the protected oxime derivative. 3-Hydroxyiminobutyl benzyl ether was obtained in a yield of 90 mole %.

The results demonstrate that 3-allyloxyiminobutyl benzyl ether is useful as a protected oxime.

EXAMPLE 3

Allyl etherification (synthesis of a protected oxime compound)

The same allyl etherifying procedure as in Example 2 was repeated except that m-aminoacetophenone oxime was used as the starting material. An allyl ether of the above oxime was obtained in a yield of 85 mole %.

Carbobenzoxylation (synthesis of a protected oxime derivative)

A reactor was charged with an aliquot (0.5 mole) of m-aminoacetophenone oxime allyl ether, 2 moles of carbobenzoxy chloride, 2.5 moles of sodium hydrogen carbonate and 15 moles of acetone, and the mixture was heated under reflux for 5 hours. After the reaction, the inorganic material was removed by filtration. The filtrate was extracted in a customary manner. The crude product was purified by column chromatography to give m-carbobenzoxyaminoacetophenone oxime allyl ether in a yield of 70 mole %.

Deprotection (synthesis of an oxime derivative)

The same deprotecting procedure as in Example 1 was repeated except that m-carbobenzoxyaminoacetophenone oxime allyl ether was used as the protected oxime derivative. m-Carbobenzoxyaminoacetophenone oxime was obtained in a yield of 90 mole %.

EXAMPLE 4

The same allyl etherification as in Example 1 was repeated except that crotyl bromide was used as the allylating agent. The corresponding crotyl ether was obtained in a yield of 78 mole %. Deprotection gave 2-methyl-5-hydroxyimino-2-heptene in a yield of 85 mole %.

EXAMPLE 5

A reactor was charged with 0.5 mole of allyloxyiminocyclohexane synthesized by the same method as in Example 1, 0.005 mole of palladium acetate, 0.02 mole of triphenylphosphine, 1.5 moles of triethylamine formate, 20 moles of ethanol and 12 moles of water. The mixture was heated under refluxing conditions and stirred for 1 hour. After the reaction, ethanol was evaporated from the reaction mixture under reduced pressure. Ten moles of methylene chloride was added to the residue, and the mixture was washed with a saturated aqueous solution of sodium chloride. The solvent was concentrated, and the residue was purified by silica gel column chromatography. Cyclohexanone oxime was obtained in a yield of 95 mole %.

A quantitative analysis of the reaction mixture by gas chromatography before purification showed that the reaction proceeded quantitatively.

EXAMPLE 6

Example 5 was repeated except that each of the palladium compounds indicated in Table 1 was used instead of palladium acetate. The results are shown in Table 1.

TABLE 1

| Run No. | Palladium compound | Yield of the final product (mole %) |
| --- | --- | --- |
| 1 | palladium acetylacetonate | 90 |
| 2 | tris(dibenzylidenedi- | 92 |

TABLE 1-continued

| Run No. | Palladium compound | Yield of the final product (mole %) |
| --- | --- | --- |
|  | acetone) dipalladium (0) |  |

EXAMPLE 7

Example 5 was repeated except that each of the formic acid compounds indicated in Table 2 was used instead of triethylamine formate. The results are shown in Table 2.

TABLE 2

| Run No. | Formic acid compound | Yield of the final product (mole %) |
| --- | --- | --- |
| 1 | formic acid | 90 |
| 2 | pyridine formate | 95 |
| 3 | ammonium formate | 70 |

EXAMPLE 8

Example 5 was repeated except that each of the ligands indicated in Table 3 was used instead of riphenylphosphine, and the reaction was carried out for each of the periods indicated in Table 3. The results are shown in Table 3.

TABLE 3

| Run No. | Ligand | Reaction time (hours) | Yield of the final product (mole %) |
| --- | --- | --- | --- |
| 1 | tri-n-butyl-phosphine | 1 | 95 |
| 2 | triphenyl phosphite | 6 | 75 |
| 3 | α,β-ethylenedi-(diphenyl)phosphine | 1 | 90 |

EXAMPLE 9

Example 5 was repeated except that each of the starting compounds indicated in Table 4 was used as the starting material. The results are shown in Table 4.

In the structural formulae of the starting materials and products indicated in Table 4, the straight line represents a carbon-carbon bond; Me represents a methyl group; and a hydrogen atom bonded to a carbon atom is omitted.

TABLE 4

| Run No. | Starting material | Product | Yield (mole %) |
| --- | --- | --- | --- |
| 1 | 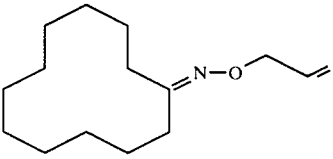 | 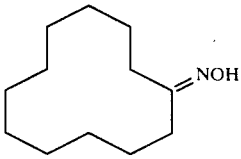 | 95 |
| 2 | 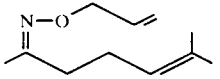 | 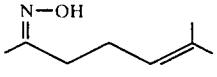 | 96 |

TABLE 4-continued

| Run No. | Starting material | Product | Yield (mole %) |
|---|---|---|---|
| 3 | 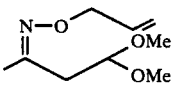 | 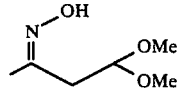 | 94 |
| 4 | 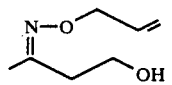 | 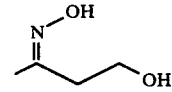 | 95 |
| 5 | 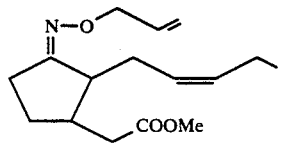 | 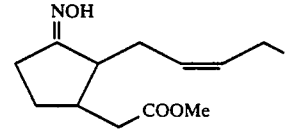 | 92 |
| 6 | 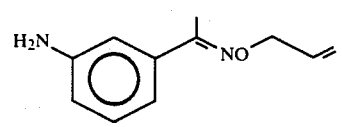 | 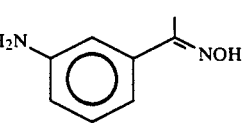 | 95 |
| 7 | 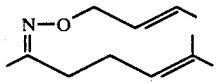 | 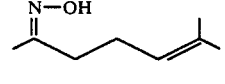 | 85 |

EXAMPLE 10

Example 5 was repeated except that 5 moles of triethylamine acetate was used instead of 1.5 moles of triethylamine formate. The reaction mixture was concentrated to remove the solvent, and the residue was purified by silica gel chromatography to give cyclohexanone oxime in a yield of 51 mole %.

A quantitative analysis of the reaction mixture by gas chromatography before purification showed that the selectivity of the reaction was quantitative.

EXAMPLE 11

Example 10 was repeated except that each of the palladium compounds indicated in Table 5 was used instead of palladium acetate. The results are shown in Table 5.

TABLE 5

| Run No. | Palladium compound | Yield (mole %) | Selectivity (mole %) |
|---|---|---|---|
| 1 | palladium acetylacetonate | 48 | 95 |
| 2 | tris(dibenzylidenediacetone) dipalladium (0) | 49 | 95 |

EXAMPLE 12

Example 1 was repeated except that each of the nucleophilic reagents indicated in Table 6 was used instead of triethylamine acetate. The results are shown in Table 6.

TABLE 6

| Run No. | Nucleophilic reagent | Yield (mole %) | Selectivity (mole %) |
|---|---|---|---|
| 1 | acetic acid | 25 | 90 |
| 2 | pyridine acetate | 50 | 95 |
| 3 | sodium salt of methyl acetoacetate | 54 | 92 |
| 4 | triethylamine propionate | 45 | 95 |
| 5 | sodium phenoxide | 58 | 85 |

EXAMPLE 13

Example 10 was repeated except that each of the ligands indicated in Table 7 was used instead of triphenylphosphine, d the reaction was carried out for each of e periods indicated in Table 7. The results are shown in Table 7.

TABLE 7

| Run No. | Ligand | Reaction time (hours) | Yield (mole %) | Selectivity (mole %) |
|---|---|---|---|---|
| 1 | tri-n-butylphosphine | 1 | 50 | 95 |
| 2 | triphenyl phosphite | 6 | 45 | 93 |
| 3 | α,β-ethylenedi-(diphenyl)phosphine | 1 | 49 | 94 |

EXAMPLE 14

Example 10 was repeated except that each of the starting compounds indicated in Table 8 was used as the starting material. The results are shown in Table 8.

5 In the structural formulae of the starting materials and products indicated in Table 8, the straight line represents a carbon-carbon bond; Me represents a methyl group; and a hydrogen atom bonded to a carbon atom is omitted.

TABLE 8

| Run No. | Starting material | Product | Yield (mole %) | Selectivity (mole %) |
|---|---|---|---|---|
| 1 | | | 53 | 97 |
| 2 | | | 50 | 93 |
| 3 | | | 47 | 90 |
| 4 | | | 55 | 90 |
| 5 | | | 50 | 96 |
| 6 | | | 48 | 92 |
| 7 | | | 58 | 93 |

What is claimed is:

1. A process for deprotecting a protected oxime compound in a single step reaction comprising contacting a protected oxime compound containing a hydroxyimino group protected by a 2-alkenylating group, with a catalyst of a platinum-group metal compound in the presence of a nucleophilic reagent.

2. The process of claim 1 wherein the 2-alkenylating group is derived from a compound which reacts with the hydroxyimino group to convert it into a 2-alkenyloxyimino group and is represented by the general formula

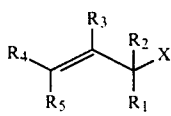

wherein each of $R_1$, $R_2$, $R_3$, $R_4$ and $R_5$ represents hydrogen or hydrocarbon group which may have a substituent, and X represents a halogen atom, or a residue of a sulfonic acid.

3. The process of claim 1 wherein the 2-alkenylating group is derived from a compound in which the 2-alkenyl moiety has not more than 10 carbon atoms.

4. The process of claim 1 wherein the oxime compound has a molecular weight of not more than 5,000.

5. The process of claim 1 wherein the oxime compound contains not more than 100 carbon atoms.

6. The process of claim 1 wherein the oxime compound is aliphatic, alicyclic, aromatic or heterocyclic.

7. The process of claim 1 wherein the catalyst is composed of the compound of a platinum-group metal and a ligand.

8. The process of claim 7 wherein the ligand is an electron donor compound having a metal of Group V of the periodic table as a coordination atom.

9. The process of claim 8 wherein the electron donor compound is a phosphorus-containing compound.

10. The process of claim 1 wherein the compound of a platinum-group metal is a salt or complex of palladium, ruthenium platinum or rhodium.

11. The process of claim 10 wherein the compound of a platinum-group metal is a salt or complex of palladium.

12. The process of claim 11 wherein the palladium salt or complex is a 0-valent or divalent compound of palladium.

13. The process of claim 1 wherein the catalyst is used in a proportion of 0.01 to 10 moles per 100 moles of the protected oxime compound.

14. The process of claim 1 wherein the nucleophilic reagent is used in a proportion of at least one molecule per protected oxime in the protected oxime compound.

15. The process of claim 1 wherein the contacting is carried out in the presence of a diluent.

16. The process of claim 15 wherein the diluent comprises a nitrile, amide, ether or alcohol in such a proportion that the concentration of the protected oxime compound is 1 to 50% by weight.

17. The process of claim 1 wherein the contacting is carried out at a temperature of at least 20° C. for 5 minutes to 24 hours.

18. The process of claim 1 wherein the oxime compound contains at least one additional functional group selected from the group consisting of an hydroxyl group, an amino group, a cyano group, a sulfonyl group, a sulfone group, an ether linkage, a thioether linkage and an acid amide linkage.

19. The process of claim 1 wherein the 2-alkenylating group is an allyl group, methallyl group, crotyl group, cinnamyl group, prenyl group, 2-pentenyl group, 2-ethyl-2-butenyl group, p-chlorocinnamyl group, geranyl group, neryl group or lower alkoxy derivative of any these groups.

20. The process of claim 1 wherein the nucleophilic reagent is used in a proportion of from 2 to 10 molecules, per protected oxime in the protected oxime compound.

21. The process of claim 1 wherein the contacting is carried out at a temperature of from 50° to 150° C. for 5 minutes to 24 hours.

22. A process for producing an oxime derivative, which comprises protecting the hydroxyimino group of an oxime compound with a 2-alkenylating agent, subjecting the protected oxime compound to a given reaction, and thereafter deprotecting the reaction product in the presence of a nucleophilic reagent using a compound of a platinum-group metal as a catalyst, wherein the nucleophilic reagent is a lower fatty acid or its salt, an alkali metal salt of a phenol, or an alkali metal salt of a 1,3-dicarbonyl compound.

23. The process of claim 22 wherein the lower fatty acid is a fatty acid having 1 to 3 carbon atoms.

24. The process of claim 22 wherein the nucleophilic reagent is formic acid or its salt.

25. The process of claim 24 wherein the nucleophilic reagent is an organic amine salt of formic acid.

26. A single step method for deprotecting a protected oxime compound wherein said oxime compound contains up to about 50 carbon atoms and a hydroxyimino group protected by a 2-alkenylating group in which the alkenyl moiety thereof has not derived from a compound which will react with the hydroxyimino group to convert it into a 2-alkenyloxyimino group and is represented by the formula

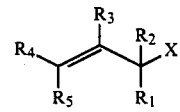

wherein each of $R_1$, $R_2$, $R_3$, $R_4$ and $R_5$ represents hydrogen or hydrocarbon group which may have a substituent, and X represents a halogen atom, or a residue of a sulfonic acid, said deprotection method comprising contacting the protected oxime compound at a temperature of from about 50° to 150° C. for from about 5 minutes to 24 hours with from about 0.1 to 5 moles, per mole of the protected oxime compound, of a catalyst comprising a compound of a platinum-group metal and at least 1 mole, per mole of the platinum group metal compound, of a ligand comprising an electron donor compound of a metal of Group V of the Periodic Table in the presence of from 2 to 10 molecules, per protected oxime of a nucleophilic reagent selected from the group consisting of lower fatty acids, salts of lower fatty acids, alkali metal salts of phenols and alkali metal salts of 1,3-dicarbonyl compounds and a diluent selected from the group consisting of nitriles, amides, ethers and alcohols, in an amount such that the concentration of the protected oxime compound is from 1 to 50% by weight.

* * * * *

UNITED STATES PATENT AND TRADEMARK OFFICE
CERTIFICATE OF CORRECTION

PATENT NO. : 4,906,768

DATED : March 6, 1990

INVENTOR(S) : TOSHIHIRO YAMADA, ET AL.

It is certified that error appears in the above-identified patent and that said Letters Patent is hereby corrected as shown below:

Column 14:

Claim 26, line 11, after "not", insert --more than 10 carbon atoms, said 2-alkenylating group being--.

Signed and Sealed this

Twenty-eighth Day of May, 1991

Attest:

HARRY F. MANBECK, JR.

*Attesting Officer*    *Commissioner of Patents and Trademarks*